United States Patent [19]

Dabrowski et al.

[11] Patent Number: 4,528,116
[45] Date of Patent: Jul. 9, 1985

[54] LIQUID CRYSTALLINE CYCLOHEXYLBENZENE DERIVATIVES THEIR PREPARATION AND THE LIQUID COMPOSITIONS CONTAINING SAME

[75] Inventors: Roman Dabrowski; Jerzy Dziaduszek; Tomasz Szczuci ski; Zofia Stolarz; Jerzy Zieli ski; Krystyna Kenig, all of Warsaw, Poland

[73] Assignee: Wojskowa Akademia Techniczna Im., Warsaw, Poland

[21] Appl. No.: 594,860

[22] Filed: Mar. 29, 1984

[30] Foreign Application Priority Data

Mar. 30, 1983 [PL] Poland ................ 241286
Mar. 30, 1983 [PL] Poland ................ 241288

[51] Int. Cl.$^3$ .......... C09K 3/34; G02F 1/13; C07C 161/04
[52] U.S. Cl. .......... 252/299.63; 252/299.5; 252/299.61; 252/299.66; 260/454; 350/350 R; 350/350 S
[58] Field of Search ........ 260/454; 252/299.63, 252/299.66, 299.5, 299.61; 350/350 R, 350 S

[56] References Cited

U.S. PATENT DOCUMENTS 3,947,375  3/1976  Gray et al. ............ 252/299.66
4,130,502 12/1978  Eidenschink et al. .... 252/299.63

FOREIGN PATENT DOCUMENTS 130269 12/1968 Czechoslovakia ........ 260/454
2636684  2/1978 Fed. Rep. of Germany ........ 252/299.63
1433130  4/1976 United Kingdom ...... 252/299.66

OTHER PUBLICATIONS

Dabrowski, R., et al., Mol. Cryst. Liq. Cryst., vol. 87 (1-2), pp. 109-135 (1982).
Van der Veen, J., J. Phys. (Paris), Colloq., (3), pp. 13-15 (1976).

Primary Examiner—Teddy S. Gron

[57] ABSTRACT

Novel 4-/trans-4'-n-alkylcyclohexyl/-1-isothiocyanatobenzenes expressed by the general formula

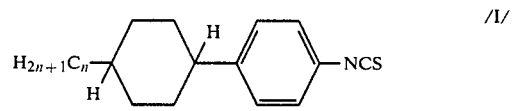

/I/ where n is an integer number from 1 to 12, method of their preparation and liquid crystal composition containing these novel compounds revealing a wide nematic phase range and low viscosity.

5 Claims, 1 Drawing Figure

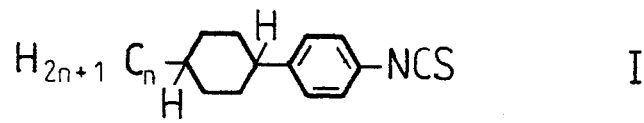
Formula
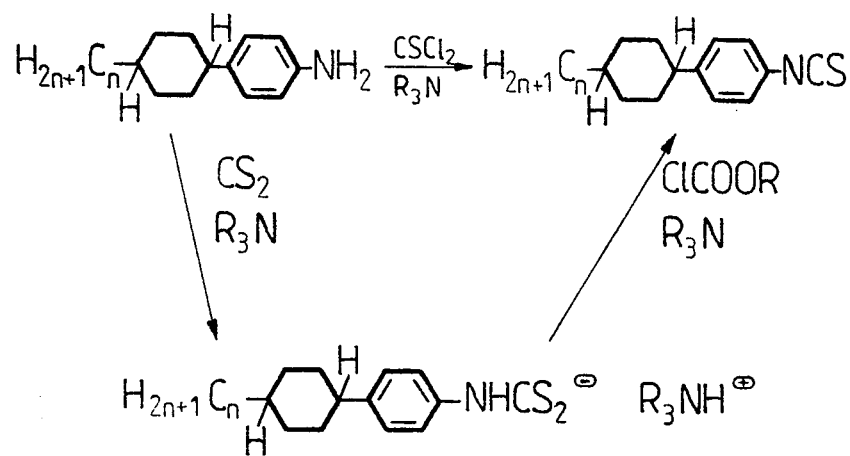
Scheme

LIQUID CRYSTALLINE CYCLOHEXYLBENZENE DERIVATIVES THEIR PREPARATION AND THE LIQUID COMPOSITIONS CONTAINING SAME

This invention relates to liquid crystalline cyclohexylbenzene derivatives, methods of their preparation and liquid-crystal compositions containing them.

Binuclear liquid-crystal compounds are known which reveal nematic properties but do not posses central groups. In this group of compounds we have derivatives of biphenyl, cyclohexylbenzene and bicyclohexyl with an alkyl or alkoxy group in one terminal position and a cyano group in the other /see patent specifications: GB Pat. No. 1 433 130, U.S. Pat. No. 3,947,375, GFR Pat. No. 2 636 684/. These compounds have melting temperatures in the range 20°–40° C. and nematic to isotropic phase transition temperatures in the range 30°–80° C. They have gained considerable significance as components of liquid crystal compositions used in display devices.

The alkyl or alkoxy derivatives of biphenyl, cyclohexylbenzene or bicyclohexyl having in the second terminal position of the molecule such groups as e.g. —$NO_2$, halogen or alkoxy instead of the cyano one do not reveal advantageous properties as they either reveal no liquid-crystalline properties or have usually only highly ordered smectic phases. For instance 4-pentyl-4'-bromobiphenyl melts at 94.5° C. and is not a liquid crystal, 4-pentyl-4'-pentanoylbiphenyl is a smectic B with phase transition temperatures C 106 $S_B$ 110.5 I, while 4.4'-dipentylbiphenyl has smectic E and B phases /$S_E$ 47 $S_B$ 52 I/. The properties of the above mentioned as well as of other 4'-substituted pentylbiphenyls have been described in Mol.Cryst. Liq.Cryst., 88, 55 /1982/.

So far no nematic liquid crystal compounds with the isothiocyanate /—N=C=S/ group are known. In the literature only one such compound has been mentioned, viz. 4-pentyl-4'-isothiocyanatobiphenyl, which reveals a highly ordered smectic E phase only. Studies have shown that also other compounds belonging to this homologous series have no nematic properties but reveal the presence of highly viscous smectic phases or are not mesomorphic.

Unexpectedly it has been found, however, that if one of the benzene rings in 4-alkyl-4'-isothiocyanatobiphenyl is replaced by a saturated cyclohexane ring, then novel liquid-crystalline compounds obtained possessing a nematic phase.

The invention relates to 4-/trans-4'-n-alkylcyclohexyl/-1-isothiocyanatobenzenes which are novel compounds whose structure is expressed by the general formula:

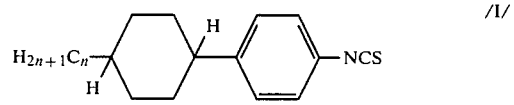

where n is an integer number from 1 to 12. In these compounds the phenyl and alkyl groups are located in positions 1 and 4 of the cyclohexane ring in the trans position. These compounds are useful as components of liquid-crystalline materials applied in display elements, their presence causing the extending of the range of the nematic phase and lowering of the viscosity of those materials.

The compounds of the present invention expressed by the general formula /I/ are obtained by treating 4-/trans-4'-n-alkylcyclohexyl/anilines with an alkyl with 1 to 12 carbon atoms in the chain with acid chlorides /preferably thiophosgene/ or alkyl chloroformate in an organic solvent solution /preferably benzene/ in the presence of a ternary amine /preferably triethylamine/ and carbon disulphide. If the alkyl chloroformate /especially ethyl chloroformate/ is used, it is advantageous to conduct the reaction in two steps. In the first one 4-/trans-4'-n-alkylcyclohexyl/aniline with a $C_1$–$C_{12}$ alkyl in organic solvent /preferably benzene/ solution is treated with carbon disulphide in the presence of ternary amine /desirably triethylamine/. The crystalline trialkylammonium dithiocarbamate obtained in the reaction is separated by filtration. In the second step this product is treated with alkyl chloroformate, e.g. ethyl chloroformate, in the presence of a ternary amine. In this reaction dithiocarbamate is converted to the isothiocyanate of formula /I/.

The final product obtained by the above method has higher purity than the one obtained in the one-step process. The product obtained both in the one-step and two-step process is isolated by conventional methods.

The scheme of the reaction according to the invention both in the one-step and two-step modifications is given below and in the FIGURE:

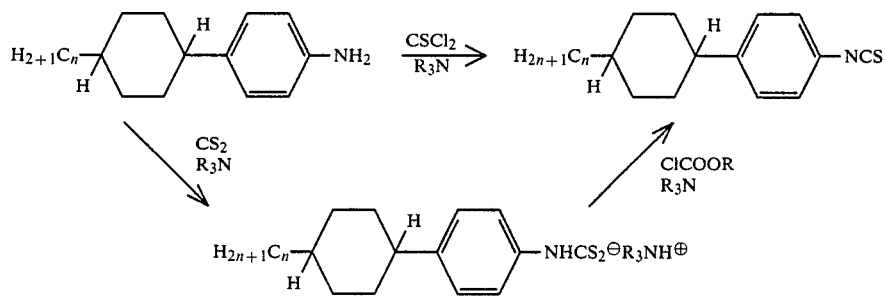

where R is the alkyl group.

The isothiocyanates of the present invention reveal a nematic phase of stability similar to that of the analogous, mentioned at the beginning of this description, compounds with the cyano group, however in distinction to the cyano derivatives they often have a wider range of the nematic phase, since some of the compounds of the present invention have low melting temperatures. Particularly advantageous properties are revealed by the compound with the hexyl group, i.e. by the compound expressed by formula /I/ with n=6, whose solid phase converts into the nematic phase in the temperature range 11.5° to 12.5° C. This compound is also characterized by low viscosity $\eta_{20°} = 21$ mPa.s. The analogous compound with the cyano group melts to the nematic phase only at 42° C.

The compounds obtained according to the present invention are nematics revealing positive dielectric anisotropy $\Delta\epsilon = +7.5$.

The table below summarizes the phase transition temperatures for several representatives of the 4-/trans-4'-n-alkylcyclohexyl/-1-isothiocyanatobenzene series obtained according to the method of the present invention /column A/ and of the analogous isothiocyanato derivatives of biphenyl in the form of 4-/4'-n-alkylphenyl/-1-isothiocyanatobenzene /column B/. The alkyl groups specified in the table relate both to compounds A and B.

TABLE

| No. | Alkyl | Phase transition temperature, °C. | |
|---|---|---|---|
| | | A | B |
| 1 | $C_2H_5$ | C 23 I/−4 N/ | |
| 2 | $C_3H_7$ | C 38.5 N 41.5 I | |
| 3 | $C_4H_9$ | C 34.5 I/32 N/ | |
| 4 | $C_5H_{11}$ | C 67.5*I/49.5 N/ | C 53 $S_E$ 74.5 I |
| 5 | $C_6H_{13}$ | C 12.5 N 43.0 I | $S_E$ 77 I |
| 6 | $C_7H_{15}$ | C 37.0 N 52 I | C 56 $S_E$ 73 I |
| 7 | $C_8H_{17}$ | C 28 N 48 I | |
| 8 | $C_{10}H_{21}$ | C 42 N 50 I | | where
C — solid,
N — nematic phase,
I — isotropic phase,
$S_E$ — smectic E phase.
*The metastable solid form of this compound melts at 36° C.

The present invention also includes liquid-crystalline compositions containing compounds of formula /I/.

As it has already been mentioned, 4-/trans-4'-n-alkylcyclohexyl/-1-isothiocyanatobenzenes successfully lower the viscosity of liquid-crystalline mixtures and allow to obtain mixtures melting at lower temperatures than for instance the mixtures including alkylcyclohexylcyanobenzenes of similar structure.

The compositions of the present invention present an at least binary systems including 4-/trans-4'-n-alkylcyclohexyl/-1-isothiocyanatobenzene of formula I as at least one of the components.

Using as a component or as components of a given composition compounds of formula I we obtain liquid-crystalline mixtures melting to the nematic phase at temperatures lower than in the case of mixtures including an addition of alkylcyclohexylcyanobenzenes. This greater efficiency is due to that the 4-/trans-4'-n-alkylcyclohexyl/-1-isothiocyanatobenzene series melt to the nematic phase at lower temperatures as compared with 4-/trans-4'-n-alkylcyclohexyl/-cyanobenzenes. For instance 4-/trans-4'-n-hexylcyclohexyl/-1-isothiocyanatobenzene phases from the solid to the nematic phase at 12.5° C., while 4-/trans-4'-n-hexylcyclohexyl/-1-cyanobenzene converts to the nematic phase only at 42° C., and the lowest melting compound in the homologous series, 4-/trans-4'-n-pentylcyclohexyl/-1-cyanobenzene, assumes the nematic phase at 30° C.

The composition of the present invention may consist solely of compounds of the 4-/trans-4'-n-alkylcyclohexyl/-1-isothiocyanatobenzenes as well as of mixtures of these compounds with other conventional liquid crystal compounds.

From the group of isothiocyanato compounds it is particularly advantageous to use in the compositions of the present invention 4-/trans-4'-n-propylcyclohexyl/-1-isothiocyanatobenzene and/or 4-/trans-4'-n-hexylcyclohexyl/-1-isothiocyanatobenzene.

As regards the conventional liquid crystal compounds, the composition of the present invention may include, e.g., 4-alkyl-4'-cyanobisphenyls and/or 4-alkoxy-4'-cyanobiphenyls and/or 4-alkoxy-4'-cyanobiphenyls and/or esters of 4-alkylbenzoic acids and/or esters of 4-alkoxybenzoic acids and/or esters of cycloalkanecarboxylic acids and/or 4-/alkylcyclohexyl/cyanobenzenes and/or Schiff bases and/or azoxy compound and/or 2,5-disubstituted 1,3-dioxane derivatives and/or optically active compounds.

The compositions of the present invention are suitable for use in display elements.

The examples which follow illustrate the methods of production of the novel compounds expressed by formula /I/ as well as those of obtaining liquid-crystalline compositions, however, without limiting the range of the invention.

EXAMPLE 1

Synthesis of 4-/trans-4'-n-hexylcyclohexyl/-1-isothiocyanatobenzene

In a conical flask with a mixture of 80 cm³ of benzene and 20 cm³ of hexane 25.8 g /0.1 mole/ of 4-/trans-4'-n-hexylcyclohexyl/aniline is dissolved. Next 7.5 cm³ /0.1 mole/ of carbon disulphide and 15 cm³ of triethylamine are added and the flask is left to stand for 45 hours at 0° C. The yellow triethylammonium dithiocarbamate precipitate is filtered, washed with hexane and dried. The crystals are transferred to a three-necked flask, 100 cm³ of chloroform and 15.5 cm³ of triethylamine are added upon which 15.5 cm³ of ethyl chloroformate are added dropwise while mixing. Next the contents are cooled down to ambient temperature and poured into 3N hydrochloric acid. After distilling off chloroform, the residual oil is recrystallized from ethanol.

15 g of 4-/Trans-4'-n-hexylcyclohexyl/-1-isothiocyanatobenzene with phase transition temperatures C 12.5N 43.0 I is obtained.

EXAMPLE 2

Synthesis of 4-/trans-4'-n-propylcyclohexyl/-1-isothiocyanatobenzene

In a three-necked flask 21.54 /0.1 mole/ of 4-/trans-4'-propylcyclohexyl/aniline in 100 cm³ of chloroform is dissolved, next 15 cm³ of triethylamine is added and 7.55 cm³ /0.1 mole/ of thiophosgene is introduced by dropwise. The contents are agitated for 10 hours upon which the mixture is poured into 3N hydrochloric acid. The product is isolated like in example 1. The yield of 4-/trans-4'-n-propylcyclohexyl/-1-isothiocyanatobenzene is 17.5 g, phase transition temperatures C 38.5N 41.5 I.

EXAMPLE 3

Liquid-crystalline composition being a binary eutectic of the composition:
4-/trans-4'-n-propylcylohexyl/-1-isothiocyanatobenzene: 42.9% wt.
4-/trans-4'-n-hexylcyclohexyl/-1-isothiocyanatobenzene: 57.1% wt.
Parameters of the composition:
  melting point: −3° C.
  clearing point: 41° C.

viscosity at 20° C.: 13.5 mPa.s
For comparison: the eutectic composed of alkylcyclohexylcyanobenzenes with alkyl chains of the same length, including:
4-/trans-4'-n-propylcyclohexyl/-1-cyanobenzene: 64.7% wt.
4-/trans-4'-n-hexylcyclohexyl/-1-cyanobenzene: 35.3% wt.
melts at 11.5° C.
and the lowest melting binary eutectic mixture in the alkylcyclohexylcyanobenzene homologous series of the composition:
4-/trans-4'-n-pentylcyclohexyl/-1-cyanobenzene: 53.4% wt.
4-/trans-4'-n-heptylcyclohexyl/-1-cyanobenzene: 46.6% wt.
melts at 7.5° C.

EXAMPLE 4

Liquid-crystalline composition constituting a binary eutectic of the composition:
4-pentyl-4'-cyanobiphenyl: 45.5% wt.
4-/trans-4'-n-hexylcyclohexyl/-1-isothiocyanatobenzene: 54.4% wt.
melts at −4° C.
For comparison: the binary eutectic consisting of 4-pentyl-4'-cyanobiphenyl and the most suitably selected 4-alkylcyclohexyl-1-cyanobenzene of the composition:
4-pentyl-4'-cyanobiphenyl: 55.0% wt.
4-/trans-4'-n-pentylcyclohexyl/-1-cyanobenzene: 45.0% wt.
melts at −0.5° C.

EXAMPLE 5

Quaternary composition containing:
4-/trans-4'-n-propylcyclohexyl/-1-isothiocyanatobenzene: 29.5% wt.
4-/trans-4'-n-pentylcyclohexyl/-1-isothiocyanatobenzene: 32.8% wt.
4-/trans-4'-n-hexylcyclohexyl/-1-isothiocyanatobenzene: 27.5% wt.
4-/trans-4'-n-octylcyclohexyl/-1-isothiocyanatobenzene: 10.2% wt.
Parameters of the composition:
melting point: −18° C.
clearing point: 43° C.
dielectric anisotropy: $\Delta\epsilon_{20°} = +7.5$

EXAMPLE 6

Liquid-crystalline quaternary composition having the composition:
4-/trans-4'-n-propylcyclohexyl/-1-isothiocyanatobenzene: 26.56% wt.
4-/trans-4'-n-hexylcyclohexyl/-1-isothiocyanatobenzene: 19.50% wt.
4-pentyl-4'-cyanobiphenyl: 24.81% wt.
4-/trans-4'-n-propylcyclohexyl/-1-cyanobenzene: 29.13% wt.
Parameters of the composition:
melting point: −27° C.
clearing point: 42° C.

EXAMPLE 7

Mixture A is first prepared consisting of:
4'-cyanophenyl 4-n-butylbenzoate: 18.85% wt.
4'-cyanophenyl 4-n-pentylbenzoate: 19.82% wt.
4'-cyanophenyl 4-n-hexylbenzoate: 20.75% wt.
4'-cyanophenyl 4-n-heptylbenzoate: 21.72% wt.
4'-butyl 4-cyanobenzoate: 18.86% wt.
Next liquid-crystalline composition was prepared having the composition:
mixture A: 59.40% wt.
4-/trans-4'-n-hexylcyclohexyl/-1-isothiocyanatobenzene: 24.75% wt.
4''-cyanophenyl 4-/trans-4'-n-pentylcyclohexyl/benzoate: 14.85% wt.
4'-nitrophenyl 4-/2-methylbutyloxycarboxy/benzoate /optic.active/: 1.0% wt.
Parameters of the composition:
melting point −22° C.
clearing point 72.5° C.
dielectric anisotropy $\Delta\epsilon_{20°} = +14.5$

EXAMPLE 8

Liquid-crystalline composition having the composition:
mixture A /as in example 7/: 40.00% wt.
4-/trans-4'-n-propylcyclohexyl/-1-isothiocyanatobenzene: 17.14% wt.
4-/trans-4'-n-pentylcyclohexyl/-1-isothiocyanatobenzene: 9.50% wt.
4-/trans-4'-n-hexylcyclohexyl/-1-isothiocyanatobenzene: 9.96% wt.
4-/trans-4'-n-heptylcyclohexyl/-1-isothiocyanatobenzene: 10.40% wt.
4''-cyanophenyl 4-/trans-4'-n-propylcyclohexyl/benzoate: 6.00% wt.
4''-cyanophenyl 4-/trans-4'-n-pentylcyclohexyl/benzoate: 6.50% wt.
4-/2-methylbutyloxy/-4'-cyanobiphenyl /optically active/: 0.50% wt.
This liquid-crystalline composition does not freeze down to −25° C. and has its clearing point at 62° C.

EXAMPLE 9

Mixture B is first prepared consisting of:
4-/trans-4'-n-propylcyclohexyl/-1-isothiocyanatobenzene: 45.12% wt.
4-/trans-4'-n-hexylcyclohexyl/-1-isothiocyanatobenzene: 26.22% wt.
4-/trans-4'-n-octylcyclohexyl/-1-isothiocyanatobenzene: 28.66% wt.
Next a liquid-crystalline composition including mixture B was prepared having the composition:
mixture B: 45.00% wt.
4-pentyl-4'-cyanobiphenyl: 20.70% wt.
4-heptyl-4'-cyanobiphenyl: 11.66% wt.
4-hexyloxy-4'-cyanobiphenyl: 5.80% wt.
4-octyloxy-4'-cyanobiphenyl: 6.40% wt.
4''-cyanophenyl 4-/trans-4'-ethylcyclohexyl/benzoate: 10.00% wt.
4-/2-methylbutyloxy/-4'-cyanobiphenyl /optically active/: 0.50% wt.
This liquid-crystalline composition does not freeze down to −25° C. and has its clearing point at 54° C.

EXAMPLE 10

Liquid-crystalline composition having the composition:
mixture B /as in example 9/: 60.00% wt.
4''-nitrophenyl 4-/trans-4'-n-pentylcyclohexyl/benzoate: 9.00% wt.
4'-nitrophenyl 4-propylbenzoate: 22.00% wt.
4''-nitrophenyl 4-/trans-4'-n-pentylcyclohexyl/benzoate: 8.00% wt.

4'-nitrophenyl 4-/2-methylbutyloxycarboxy/benzoate /optic.active/: 1.0% wt.

This liquid-crystalline composition clears at +52° C. and freezes at −5° C.

EXAMPLE 11

Liquid-crystalline composition having the composition:
4-/trans-4'-n-propylcyclohexyl/-1-isothiocyanatobenzene: 28.03% wt.
4-ethyl-4'-cyanobiphenyl: 9.95% wt.
4-pentyl-4'-cyanobiphenyl: 34.81% wt.
4'-cyanophenyl 4-n-butylbenzoate: 4.22% wt.
4'-cyanophenyl 4-n-hexylbenzoate: 5.68% wt.
4''-cyanophenyl 4-/trans-4'-n-pentylcyclohexyl/benzoate: 7.83% wt.
4''-methylphenyl 4-/trans-4'-n-pentylcyclohexyl/benzoate: 9.48% wt.

This liquid-crystalline composition is a nematic in the temperature range −30° C. to 58° C. It has a positive dielectric anisotropy $\Delta\epsilon_{20°} = +10$, threshold voltage $U_{10\%} = 1$ V and saturation voltage $U_{90\%} = 1.6$ V.

EXAMPLE 12

Liquid-crystalline composition having the composition:
4-/trans-4'-n-propylcyclohexyl/-1-isothiocyanatobenzene: 17.06% wt.
4-/trans-4'-n-hexylcyclohexyl/-1-isothiocyanatobenzene: 27.76% wt.
4-/trans-4'-ethylcyclohexyl/-1-cyanobenzene: 7.71% wt.
4-/trans-4'-n-pentylcyclohexyl/-1-cyanobenzene: 17.18% wt.
2-/4'-cyanophenyl/-5-n-hexyl-1,3-dioxane: 6.07% wt.
4-propoxy-4'-cyanobiphenyl: 5.34% wt.
4-pentyl-4'-cyanoterphenyl: 4.57% wt.
2-[4'-/trans-4''-n-pentylcyclohexyl/phenyl]-5-n-butyl-1,3-dioxane: 9.97% wt.
2-[4'-/trans-4''-n-pentylcyclohexyl/phenyl]-5-n-pentyl-1,3-dioxane: 8.44% wt.

The composition is a nematic in the temperature range −35° C. to 70° C. It reveals positive permittivity anisotropy $\Delta\epsilon_{20°} = +6$, and viscosity $\eta_{20°} = 36$ mPa.s.

We claim:

1. 4-/trans-4'-n-alkylcyclohexyl/-1-isothiocyanatobenzenes expressed by the general formula:

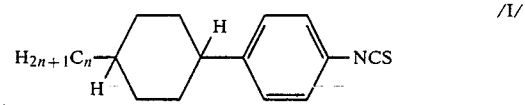

/I/ where n is an integer number from 1 to 12.

2. 4-/trans-4'-n-alkylcyclohexyl/-1-isothiocyanatobenzenes as claimed in claim 1 where n is 3 to 7.

3. Liquid crystal mixture including at least one component expressed by formula /I/ as claimed in claim 1.

4. Liquid crystal mixture as claimed in claim 3 wherein are included 4-/trans-4'-n-propylcyclohexyl/-1-isothiocyanatobenzene and/or 4-/trans-4'-n-hexylcyclohexyl/-1-isothiocyanatobenzene.

5. Liquid crystal mixture as claimed in claim 3 including a liquid crystal compound selected from the group consisting of 4-alkyl-4'-cyanobiphenyls 4-alkoxy-4'-cyanobiphenyls and/or esters of 4-alkylbenzoic acids and/or esters of 4-alkoxybenzoic acids, esters of 4-alkylcycloalkanecarboxylic acids, 4-/alkylcyclohexyl/-cyanobenzenes and/or Schiff bases, and 2,5-disubstituted 1,3-dioxane derivatives and/or optically active compounds.

* * * * *